US00PP15476P2

(12) United States Plant Patent
Brouwer

(10) Patent No.: US PP15,476 P2
(45) Date of Patent: Jan. 11, 2005

(54) ***SPATHIPHYLLUM* PLANT NAMED 'CARLOS'**

(50) Latin Name: *Spathiphyllum hybrid*
Varietal Denomination: Carlos

(75) Inventor: Wilhelmus A. J. Brouwer, Nootdorp (NL)

(73) Assignee: W.A.J. Brouwer Holding B.V., Nootdorp (NL)

( * ) Notice: Subject to any disclaimer, the term of this patent is extended or adjusted under 35 U.S.C. 154(b) by 0 days.

(21) Appl. No.: 10/766,763

(22) Filed: Jan. 28, 2004

(51) Int. Cl.[7] ..... A01H 5/00
(52) U.S. Cl. ..... Plt./364
(58) Field of Search ..... Plt./364

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Spathiphyllum* plant named 'Carlos', characterized by its compact, bushy, upright and outwardly arching plant habit; freely clumping growth habit; dark green-colored leaves; white-colored spathes and creamy white-colored spadices that are positioned above the foliage on strong and erect peduncles; and good postproduction longevity.

2 Drawing Sheets

Botanical classification/cultivar designation: *Spathiphyllum* hybrid cultivar Carlos.

BACKGROUND OF THE INVENTION

The present Invention relates to a new and distinct cultivar of *Spathiphyllum* plant, botanically known as *Spathiphyllum* hybrid, and hereinafter referred to by the cultivar name Carlos.

The new cultivar is a product of a planned and controlled breeding program conducted by the Inventor in Nootdorp, The Netherlands. The objective of the breeding program is to create new compact *Spathiphyllum* cultivars with dark green foliage, freely flowering habit and spathes held above the foliage.

The new cultivar originated from a cross-pollination made by the Inventor in June, 1998 of a proprietary *Spathiphyllum* hybrid selection identified as code number 280, not patented, as the female or seed parent and a proprietary *Spathiphyllum* hybrid selection identified as code number 109, not patented, as the male or pollen parent. The cultivar Carlos was discovered and selected by the Inventor as a single plant within the progeny of the stated cross-pollination in a controlled environment in Nootdorp, The Netherlands, in May, 1999.

Asexual propagation of the new cultivar by tissue culture since June, 1999, in a laboratory in Nootdorp, The Netherlands, has shown that the unique features of this new *Spathiphyllum* plant are stable and reproduced true to type in successive generations of asexual propagation.

SUMMARY OF THE INVENTION

The new *Spathiphyllum* has not been observed under all possible environmental conditions. The phenotype may vary somewhat with variations in environment such as temperature and light intensity without, however, any variance in genotype.

The following traits have been repeatedly observed and are determined to be the unique characteristics of 'Carlos'. These characteristics in combination distinguish 'Carlos' as a new and distinct *Spathiphyllum* cultivar:

1. Compact, bushy, upright and outwardly arching plant habit.
2. Freely clumping growth habit.
3. Dark green-colored leaves.
4. White-colored spathes and creamy white-colored spadices that are positioned above the foliage on strong and erect peduncles.
5. Good postproduction longevity.

Plants of the new *Spathiphyllum* can be compared to plants of the female parent, the proprietary selection identified as code number 280. In side-by-side comparisons conducted in Nootdorp, The Netherlands, plants of the new *Spathiphyllum* differed from plants of the female parent selection primarily in foliage color as plants of the new *Spathiphyllum* have darker green-colored leaves.

Plants of the new *Spathiphyllum* can be compared to plants of the male parent, the proprietary selection identified as code number 109. In side-by-side comparisons conducted in Nootdorp, The Netherlands, plants of the new *Spathiphyllum* differed from plants of the male parent selection in the following characteristics:

1. Plants of the new *Spathiphyllum* were bushier than plants of the male parent selection.
2. Plants of the new *Spathiphyllum* had darker green-colored leaves than plants of the male parent selection.

Plants of the new *Spathiphyllum* can be compared to plants of the *Spathiphyllum* cultivar Adagio, not patented. However, in side-by-side comparisons conducted in Nootdorp, The Netherlands, plants of the new *Spathiphyllum* differed from plants of the cultivar Adagio in the following characteristics:

1. Plants of the new *Spathiphyllum* were more compact than plants of the cultivar Adagio.
2. Plants of the new *Spathiphyllum* were bushier than plants of the cultivar Adagio.
3. Plants of the new *Spathiphyllum* had darker green-colored leaves than plants of the cultivar Adagio.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Spathiphyllum*.

The photograph on the first sheet comprises a side perspective view of a typical plant of 'Carlos' grown in a container.

The photograph at the top of the second sheet is a close-up view of typical leaves of 'Carlos'.

The photograph at the bottom of the second sheet is a close-up view of a typical inflorescence of 'Carlos'.

DETAILED BOTANICAL DESCRIPTION

The aforementioned photographs and following observations and measurements describe seven month old plants (from planting rooted tissue-cultured plantlets) grown in Nootdrop, The Netherlands, in a glass-covered greenhouse and under commercial production conditions in 12-cm containers with one plant per container. During the production of the plants, day temperatures were about 22° C. and night temperatures were about 20° C.

In the following description, color references are made to The Royal Horticultural Society Colour Chart, 2001 Edition, except where general terms of ordinary dictionary significance are used.

Botanical classification: *Spathiphyllum* hybrid cultivar Carlos.

Parentage:

*Female parent.*—Proprietary *Spathiphyllum* hybrid selection identified as code number 280, not patented.

*Male parent.*—Proprietary *Spathiphyllum* hybrid selection identified as code number 109, not patented.

Propagation:

*Type.*—By tissue culture.

*Time to initiate roots on a tissue-cultured cutting.*—About three weeks at 20 to 22° C.

*Time to produce a fully-rooted tissue-cultured plantlet.*—About seven weeks at 20 to 22° C.

*Root description.*—Primary roots, thick and fleshy; lateral branch roots, finer; primary and lateral roots white in color and abundant.

Plant description:

*Plant shape.*—Compact, upright and outwardly arching plant habit; inverted triangle.

*Growth habit.*—Erect when young, becoming outwardly arching as leaves develop. Freely clumping and bushy full appearance; about six clumps per plant; moderately vigorous.

*Plant height.*—About 47 cm from soil level to top of leaf plane and about 66 cm from soil level to spathe apices.

*Plant spread.*—About 64 cm.

*Foliage description.*—Length: About 27 cm. Width: About 11.1 cm. Shape: Narrowly ovate to narrowly elliptic. Apex: Apiculate. Base: Attenuate. Margin: Entire; slightly undulate. Aspect: Initially upright, then outwardly arching. Surface: Midrib and lateral veins sunken on upper surface and prominent on lower surface; upper surface of blade convex between veins, lower surface of blade concave between veins; upper and lower surfaces rugose. Texture, upper and lower surfaces: Somewhat leathery; glabrous and smooth. Venation pattern: Pinnate. Color: Developing leaves, upper surface: Between 139A and 143A. Developing leaves, lower surface: 146A and 146B. Fully expanded leaves, upper surface: Darker than 139A. Fully expanded leaves, lower surface: 137A. Midvein and lateral veins, upper surface: Darker than 139A. Midvein and lateral veins, lower surface: 144B. Petiole: Length: About 18.4 cm. Diameter, just below the geniculum: About 4 mm. Diameter, at soil level: About 5 mm. Geniculum length: About 3 mm. Geniculum diameter: About 4.2 mm. Geniculum aspect: Straight to slightly curved. Wing length: About 15 cm. Wing diameter: About 4 mm. Color: Petiole: Close to 137B. Geniculum: 138B. Wing: 137A to 139A.

Inflorescence description:

*Inflorescence arrangement/quantity.*—Concave spathes with spadices held above the foliage on strong and erect peduncles. About three open spathes per plant at one time; inflorescences arise from the petiole sheath.

*Time to flower.*—Plants start flowering about six months after planting rooted tissue-cultured plantlets.

*Inflorescence longevity.*—Spathes generally maintain white color for more than three weeks on the plant.

*Fragrance.*—Moderately fragrant; sweet, pleasant.

*Inflorescence buds.*—Length: About 10 cm. Diameter: About 1 cm. Shape: Columnar. Color: Close to 155A.

*Spathe.*—Length: About 17.3 cm. Width: About 3.1 cm. Shape: Elliptic. Apex: Apiculate. Base: Attenuate. Aspect: Concave. Texture, front and rear surfaces: Slightly leathery; glabrous and smooth. Color: When developing and fully developed, front and rear surfaces: 155C.

*Spadix.*—Length: About 6.3 cm. Diameter: About 1.5 cm. Shape: Columnar with obtuse apex. Color: 158B to 158C.

*Flowers.*—Quantity per spadix: About 120. Diameter: About 3 mm. Shape: Rounded. Color: 158D. Staminate flowers: Anther color: 158D. Amount of pollen: Moderate to abundant. Pollen color: 158D. Pistillate flowers: Shape Conical; pistillate flowers extend beyond the staminate flowers. Stigma color: 158B to 158C. Ovary color: 158B to 158C.

*Scapes.*—Length: About 50.1 cm. Diameter: About 4 mm. Aspect: Erect to about 10° from vertical. Strength: Strong. Color: Slightly darker than 137A.

*Fruit/seed.*—Fruit and seed production have not been observed.

Disease/pest resistance: Plants of the new *Spathiphyllum* have not been observed to be resistant to pathogens or pests common to *Spathiphyllum*.

Temperature tolerance: Plants of the new *Spathiphyllum* have been observed to tolerate temperatures from 14 to 27° C.

It is claimed:

1. A new and distinct cultivar of *Spathiphyllum* plant named 'Carlos', as illustrated and described.

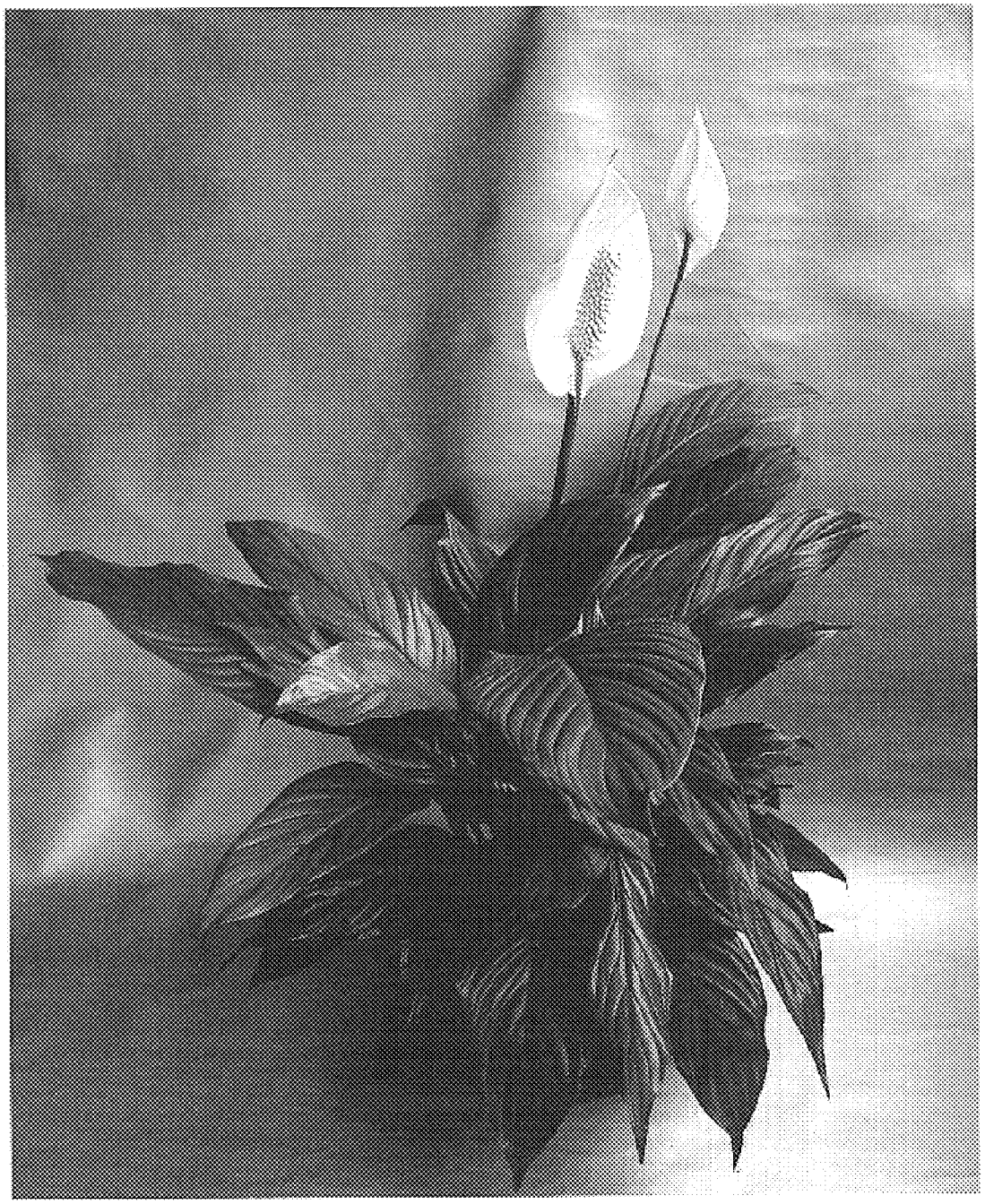

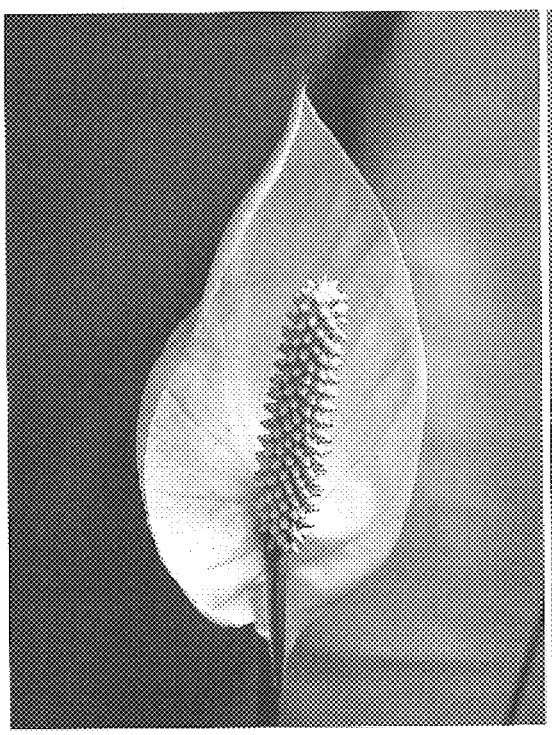
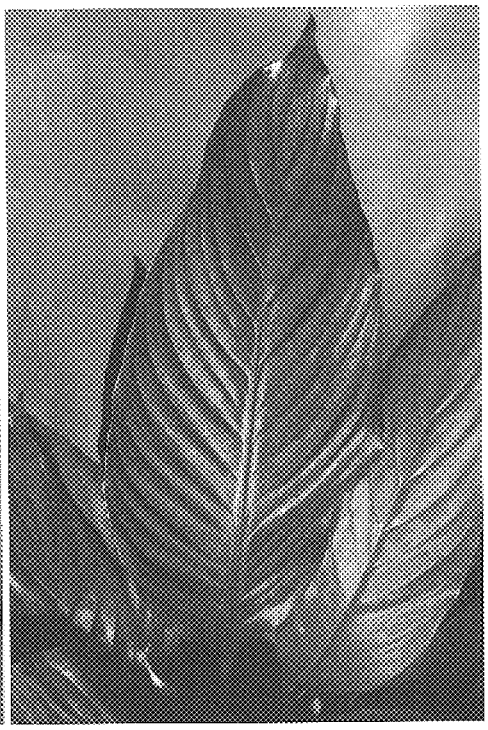

* * * * *